US 8,361,927 B2

(12) United States Patent
Wachendorff-Neumann et al.

(10) Patent No.: US 8,361,927 B2
(45) Date of Patent: Jan. 29, 2013

(54) SYNERGISTIC COMBINATION OF PROTHIOCONAZOLE AND METOMINOSTROBIN

(75) Inventors: Ulrike Wachendorff-Neumann, Neuwied (DE); Anton Kraus, Leichlingen (DE); Ingo Wetcholowsky, Langenfeld (DE); Peter Dahmen, Neuss (DE); Hiroyuki Hadano, Tochigi (JP)

(73) Assignee: Bayer CropScience AG, Monheim (DE)

( * ) Notice: Subject to any disclaimer, the term of this patent is extended or adjusted under 35 U.S.C. 154(b) by 223 days.

(21) Appl. No.: 12/973,985

(22) Filed: Dec. 21, 2010

(65) Prior Publication Data

US 2011/0160053 A1    Jun. 30, 2011

Related U.S. Application Data

(60) Provisional application No. 61/288,475, filed on Dec. 21, 2009.

(30) Foreign Application Priority Data

Dec. 21, 2009  (EP) ..................................... 09180138

(51) Int. Cl.
A01N 43/653 (2006.01)
A01N 37/50 (2006.01)
A01P 3/00 (2006.01)

(52) U.S. Cl. .................. 504/100; 514/384; 514/619

(58) Field of Classification Search .................. 504/100; 514/384, 619

See application file for complete search history.

(56) References Cited

U.S. PATENT DOCUMENTS

| | | | |
|---|---|---|---|
| 4,245,432 A | 1/1981 | Dannelly | |
| 4,272,417 A | 6/1981 | Barke et al. | |
| 4,808,430 A | 2/1989 | Kouno | |
| 5,876,739 A | 3/1999 | Turnblad et al. | |
| 7,786,148 B2 * | 8/2010 | Gouot et al. | 514/344 |
| 2002/0173529 A1 | 11/2002 | Dutzmann et al. | |
| 2003/0176428 A1 | 9/2003 | Schneidersmann et al. | |
| 2005/0101639 A1 | 5/2005 | Ammermann et al. | |
| 2006/0014738 A1 | 1/2006 | Wachendorff-Neumann et al. | |
| 2006/0035942 A1 | 2/2006 | Wachendorff-Neumann et al. | |
| 2009/0286681 A1 * | 11/2009 | Dahmen et al. | 504/100 |
| 2010/0317520 A1 * | 12/2010 | Ikeda et al. | 504/130 |
| 2012/0022021 A1 * | 1/2012 | Rademacher et al. | 514/63 |

FOREIGN PATENT DOCUMENTS

| | | |
|---|---|---|
| EP | 0 398 692 B1 | 11/1990 |
| EP | 0 737 421 A1 | 10/1996 |
| EP | 1 517 610 B1 | 4/2008 |
| WO | WO 96/16045 A1 | 5/1996 |
| WO | WO 98/47367 A1 | 10/1998 |
| WO | WO 02/28186 A2 | 4/2002 |
| WO | WO 02/080675 A1 | 10/2002 |
| WO | WO 03/073852 A2 | 9/2003 |
| WO | WO 04/000020 A1 | 12/2003 |
| WO | WO 04/000022 A1 | 12/2003 |

OTHER PUBLICATIONS

European Search Report for EP Application No. EP 09 18 0138, Munich, Germany, mailed on Apr. 22, 2010.
International Search Report for International Patent Application No. PCT/EP2010/070093, European Patent Office, Netherlands, mailed on Jul. 6, 2011.
Written Opinion of the International Search Report for International Patent Application No. PCT/EP2010/070093, European Patent Office, Netherlands, mailed on Jul. 6, 2011.
English language Abstract of Patent Publication No. WO 96/16045 A1, European Patent Office, espaceet database—Worldwide (2012).

* cited by examiner

Primary Examiner — John Pak
(74) Attorney, Agent, or Firm — Sterne, Kessler, Goldstein & Fox P.L.L.C.

(57) ABSTRACT

Combination comprising Prothioconazol and Metominostrobin preferably as a mixture, agrochemical formulation or composition for curatively and/or preventively controlling phytopathogenic fungi and/or microorganisms of plants and crops.

7 Claims, No Drawings

SYNERGISTIC COMBINATION OF PROTHIOCONAZOLE AND METOMINOSTROBIN

The invention relates to an active compound combination which comprises Prothioconazole and Metominostrobin as well as the use of Prothioconazole and Metominostrobin, preferably as a mixture, agrochemical formulation or composition for curatively or preventively controlling the phytopathogenic fungi and/or plant damaging microorganisms and/or nematodes which occur in the agricultural field. Moreover, the invention relates to a method for curatively or preventively controlling phytopathogenic fungi and/or plant damaging microorganisms and/or nematodes by using Prothioconazole and Metominostrobin, preferably as a mixture, agrochemical formulation or composition.

The triazole-type fungicide (2-[2-(1-chlorocyclopropyl)-3-(2-chlorophenyl)-2-hydroxypropyl]-2,4-dihydro-[1,2,4]-triazole-3-thione (Prothioconazole) having the following formulae

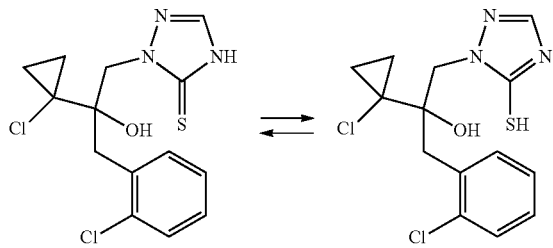 [SMILES: OC(Cc1ccccc1Cl)(Cn1nc[nH]c1=S)C1(Cl)CC1 ; OC(Cc1ccccc1Cl)(Cn1ncnc1S)C1(Cl)CC1]

and the strobilurine-type fungicide (E)-α-(methoxyimino)-N-methyl-2-phenoxy-benzeneacetamide (Metominostrobin) having the following formula

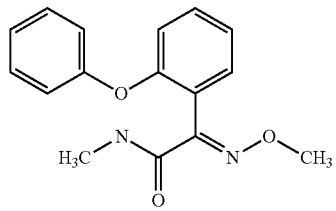 [SMILES: CNC(=O)/C(=N/OC)c1ccccc1Oc1ccccc1]

are generally known as being plant protection agents. Prothioconazole and its biological activity have been firstly described in WO 1996/16048. Metominostrobin and its biological activity are known from EP-A2-0398692. The activity of either Prothioconazole or Metominostrobin is good; however there is a constant need to develop new plant protection agents having improved properties in view of spectrum of action, toxicity, selectivity, application rate, formation of residues, and which can solve problems with resistances.

WO 2004/000020 describes a 3-way mixture containing the strobilurine-type fungicide Trifloxystrobin, and two triazole-type fungicides, namely Prothioconazole and Tebuconazole in a specific mixing ratio, which may be used for combating unwanted fungi.

EP-A1-1517610, also published as WO 2004/000022, describes a 3-way mixture containing two strobilurines-type fungicides, namely Trifloxystrobin and Fluoxastrobin and the triazole-type fungicide Prothioconazole in a specific mixing ratio, which may be used for combating unwanted fungi.

EP-A1-0737421 discloses a very general concept of combining compounds of general formula (I) with azole type fungicidal compounds or cyclic amine type fungicidal compounds. Among the compounds disclosed therein are Metominostrobin (=compound (If)) and Prothioconazole.

Several combinations containing Prothioconazole and one of the following strobilurine-type fungizides Azoxystrobin, Kresoximmethyl, Fluoxastrobin, Trifloxystrobin, Picoxystrobin, Pyraclostrobin, Dimoxystrobin and Orysastrobin have been also described in WO 1998/47367 and WO 2003/073852. However, these documents do not mention Metominostrobin.

The inventors now found that an active compound combination comprising Prothioconazole and Metominostrobin, preferably as a mixture, agrochemical formulation or composition has improved properties when compared with Prothioconazole and Metominostrobin alone, particularly this combination shows excellent results when being used for curatively and/or preventively controlling the phytopathogenic fungi and/or microorganisms of plants and crops.

It is understood that the term "active compound combination" does not encompass storerooms or laboratories wherein the two compounds are stored separately. The term "active compound combination" preferably refers to mixtures, formulations and compositions containing Prothioconazole and Metominostrobin.

In an embodiment of the invention the combination just contains Prothioconazole and Metominostrobin as agrochemically active compounds, however may contain other active ingredients, such as e.g. penetration enhancers.

In another embodiment the combination, the method of use, and the use according to the invention contains or involve Prothioconazole and Metominostrobin, preferably as the only agrochemically active ingredient, in a weight ratio in the range from 1:5 to 5:1, preferably in the range from 1:3.5 to 3.5:1, more preferably in the range from 1:2.75 to 2.75:1. Prothioconazole and Metominostrobin are preferably combined in a ratio of 1:5, 1:1.5, or 1:1.

Moreover, it has been found that combining Prothioconazole and Metominostrobin, preferably in a mixture, agrochemical formulation or composition, is useful for curatively and/or preventively controlling undesired phytopathogenic fungi (such as Plasmodiophoromycetes, Oomycota, Chytridiomycota, Zygomycota, Ascomycota, Basidiomycota and Deuteromycota) and/or microorganisms and/or nematodes which occur in the agricultural field, and thus the invention is also directed to the use of Prothioconazole and Metominostrobin, preferably as a mixture, agrochemical formulation or composition for controlling undesired fungi and/or microorganisms and/or nematodes which occur in the agricultural field.

In particular, the invention is directed to a method for curatively or preventively controlling the phytopathogenic fungi and/or microorganisms and/or nematodes which damage plants or crops and which method comprises applying Prothioconazole and Metominostrobin, preferably as a mixture, agrochemical formulation or composition to the plant (such as on the seed, plant parts or to the fruit of the plant) or to the soil in which the plant is growing or in which it is supposed to grow.

Moreover, Prothioconazole and Metominostrobin, preferably as a mixture, agrochemical formulation or composition can be used for controlling undesired fungi and/or microorganisms and/or nematodes in the protection of technical materials, and thus, the invention is directed to the use of Prothioconazole and Metominostrobin, preferably as a mixture, agrochemical formulation or composition for the protection of technical materials.

It has now been found that the combination, the method of use, and the use according to the invention not only bring about the additive enhancement of the spectrum of action with respect to the pathogen to be controlled but achieves a synergistic effect which extends the range of action, namely the rates of application of Prothioconazole and of Metominostrobin can be lowered whilst the action remains equally good, and the combination still achieves a high degree of pathogen control even where the two individual compounds have become totally ineffective in such a low application rate range. This allows a substantial broadening of the spectrum of phytopathogens that can be controlled and increased safety in disease control. Additionally, of great importance are the advantageous flexible application timing and safety in efficacy under different environmental conditions, e.g. climatic and weather conditions and disease pressures, in comparison to the single applied products Prothioconazole and Metominostrobin alone.

Moreover, besides above mentioned synergistic action, the combination, the method of use, and the use according to the invention have further advantageous properties which can also be described as synergistic activity. Examples of such advantageous properties are for example the broadening of the spectrum of activity to other phytopathogens, for example to resistant strains; adequate plant protection with the aid of the combination according to the invention, even at an application rate at which the individual compounds are totally ineffective; advantageous behavior during formulation or upon application, for example upon grinding, sieving, emulsifying, dissolving or dispensing; increased storage stability; improved stability to light; more advantageous degradability; improved toxicological or ecotoxicological behavior; improved characteristics of the plants including: emergence, crop yields, more developed root system, tillering increase, increase in plant height, bigger leaf blade, less dead basal leaves, stronger tillers, greener leaf color, less fertilizers needed, less seeds needed, more productive tillers, earlier flowering, early grain maturity, less plant verse (lodging), increased shoot growth, improved plant vigor, and early germination; or any other advantages familiar to a person skilled in the art.

A large part of the damage caused by phytopathogenic fungi and/or microorganisms and/or nematodes on cultigens occurs by infestation of the seed during storage and after sowing the seed in the ground as well as during and after germination of the plants. This phase is especially critical since the roots and shoots of the growing plant are particularly sensitive and even a small amount of damage can lead to withering of the whole plant.

It has been found that Prothioconazole and Metominostrobin, preferably as a mixture, agrochemical formulation or composition can also be used for the treatment of seed. Thus, the invention is also directed to the use of Prothioconazole and Metominostrobin, preferably as a mixture, agrochemical formulation or composition for the treatment of seed of conventional or genetically modified plants and to a method for seed treatment in which the seed is treated at the same time with Prothioconazole and Metominostrobin. It further comprises a method in which the seed is treated with Prothioconazole and Metominostrobin separately.

Prothioconazole and Metominostrobin may be mixed with other compounds, preferably agrochemically inactive compounds which enhance the usability of the combination in the agricultural field and which constitutes a fungicidal composition according to the invention.

Thus, in a further aspect, the invention is directed to the fungicidal composition comprising Prothioconazole and Metominostrobin and at least one agrochemically acceptable support, carrier or filler.

If not defined otherwise herein, the term "mixture" and "combination" stands for the various combinations of Prothioconazole and Metominostrobin, example in a single "ready-mix" form, in a combined spray mixture composed from separate formulations of the single active compounds, such as a "tank-mix", and in a combined use of the single active ingredients when applied in a sequential manner, i.e. one after the other with a reasonably short period, such as a few hours or days.

If not defined otherwise herein, the term "pathogen" stands for all organisms which cause damages on plants or any part of a plant. Pathogens are for example phytopathogenic fungi, viruses and microorganisms.

If not defined otherwise herein, the term "fungi" stands for all fungal and chromista organisms.

If not defined otherwise herein, the term "phytopathogenic fungi" stands for all fungal and chromista organisms which cause damages on plants or any part of a plant. Examples for fungal organisms are Ascomycota, Basidiomycota, Chytridiomycota, Deuteromycota, Glomeromycota, Microsporidia, Zygomycota, and anamorphic fungi. Examples for Chromista are Oomycota.

If not defined otherwise herein, the term "microorganisms" include viruses which cause damages on plants or any part of a plant (e.g. DNA, RNA, and DNA and RNA reverse transcribing viruses, and subviral agents) and furthermore stands for all bacterial and protozoan organisms (e.g. Plasmodiophoromycetes, Pseudomonadaceae, Rhizobiaceae, Enterobacteriaceae, Corynebacteriaceae and Streptomycetaceae).

If not defined otherwise herein, the term "technical material" includes paper; carpets; constructions; cooling and heating systems; wall-boards; ventilation and air conditioning systems and the like. The combinations according the present invention can prevent disadvantageous effects such as decay, discoloration or mold.

If not defined otherwise herein, the term "support" comprises a natural or synthetic, organic or inorganic compound which is inert and with which the Prothioconazole and/or Metominostrobin may be combined or associated to enhance applicability. The support may be a solid or a liquid. Examples of suitable supports include clays, natural or synthetic silicates, silica, resins, waxes, solid fertilisers, water, alcohols, in particular butanol, organic solvents, mineral and plant oils and derivatives thereof. Mixtures of such supports may also be used.

The fungicidally active composition according to the invention may also comprise additional components, such as surfactants, colouring agents or other additional (auxiliary) compounds such as e.g. protective colloids, adhesives, thickeners, thixotropic agents, penetration agents, stabilisers, sequestering agents.

The surfactant can be an emulsifier, a dispersing agent or a wetting agent of ionic or non-ionic type or a mixture of such surfactants and include for example polyacrylic acid salts, lignosulphonic acid salts, phenolsulphonic or naphthalenesulphonic acid salts, polycondensates of ethylene oxide with fatty alcohols or with fatty acids or with fatty amines, substituted phenols (in particular alkylphenols or arylphenols), salts of sulphosuccinic acid esters, taurine derivatives (in particular alkyl taurates), phosphoric esters of polyoxyethylated alcohols or phenols, fatty acid esters of polyols, and derivatives thereof containing sulphate, sulphonate and phosphate functions.

Preferably, surfactant content may be comprised from 5% to 40% by weight of the composition.

Colouring agents can be inorganic pigments, for example iron oxide, titanium oxide, ferrocyanblue, and organic pigments such as alizarin, azo and metallophthalocyanine dyes, and trace elements such as iron, manganese, boron, copper, cobalt, molybdenum and zinc salts can be used.

In general, the combination, mixture, agrochemical formulation or composition according to the invention contains from 0.05 to 99% by weight of active compounds, preferably from 10 to 70% by weight.

The combination, mixture, or composition according to the invention can be used as such, in form of their formulations or as the use forms prepared therefrom, such as aerosol dispenser, capsule suspension, cold fogging concentrate, dustable powder, emulsifiable concentrate, emulsion oil in water, emulsion water in oil, encapsulated granule, fine granule, flowable concentrate for seed treatment, gas (under pressure), gas generating product, granule, hot fogging concentrate, macrogranule, microgranule, oil dispersible powder, oil miscible flowable concentrate, oil miscible liquid, paste, plant rodlet, powder for dry seed treatment, seed coated with a pesticide, soluble concentrate, soluble powder, solution for seed treatment, suspension concentrate (flowable concentrate), ultra low volume (ULV) liquid, ultra low volume (ULV) suspension, water dispersible granules or tablets, water dispersible powder for slurry treatment, water soluble granules or tablets, water soluble powder for seed treatment and wettable powder.

The treatment of plants and plant parts with the combination, mixture, agrochemical formulation or composition according to the invention is carried out directly or by action on their environment, habitat or storage area by means of the normal treatment methods, for example by watering (drenching), drip irrigation, spraying, atomizing, broadcasting, dusting, foaming, spreading-on, and as a powder for dry seed treatment, a solution for seed treatment, a water-soluble powder for seed treatment, a water-soluble powder for slurry treatment, or by encrusting.

These combinations, mixtures, agrochemical formulations or compositions include not only those which are ready to be applied to the plant or seed to be treated by means of a suitable device, such as a spraying or dusting device, but also concentrated commercial compositions which must be diluted before application to the crop.

Within the combination, mixture, agrochemical formulation or composition according to the invention, bactericide compounds can be employed in crop protection for example for controlling Pseudomonadaceae, Rhizobiaceae, Enterobacteriaceae, Corynebacteriaceae and Streptomycetaceae.

All conventional or genetically modified plants and plant parts can be treated with the combination, mixture, agrochemical formulation or composition according to the invention. Such plant parts include propagation material such as tubers or rhizomes, and seeds, seedlings or seedlings pricking out and plants or plants pricking out, roots and over-ground parts of the plant such as trunks, stems or stalks, leaves, flowers and fruit of the concerned plant.

Examples of such plants include cotton; flax; vine; fruit or vegetable crops such as Rosaceae sp. (for instance pip fruit such as apples and pears, but also stone fruit such as apricots, almonds and peaches), Ribesioidae sp., Juglandaceae sp., Betulaceae sp., Anacardiaceae sp., Fagaceae sp., Moraceae sp., Oleaceae sp., Actimidaceae sp., Lauraceae sp., Musaceae sp. (for instance banana trees and plantins), Rubiaceae sp., Theaceae sp., Sterculiceae sp., Rutczceae sp. (for instance lemons, oranges and grapefruit); Solanaceae sp. (for instance tomatoes), Liliaceae sp., Asteraceae sp. (for instance lettuces), Umbelliferae sp., Cruciferae sp., Chenopodiaceae sp., Cucurbitaceae sp., Papilionaceae sp. (for instance peas), Rosaceae sp. (for instance strawberries); major crops such as Graminae sp. (for instance maize, lawn or cereals such as wheat, rye, rice, barley and triticale), Asteraceae sp. (for instance sunflower), Cruciferae sp. (for instance colza), Fabacae sp. (for instance peanuts), Papilionaceae sp. (for instance soybean), Solanaceae sp. (for instance potatoes), Chenopodiaceae sp. (for instance beetroots); horticultural and forest crops; as well as genetically modified homologues of these crops.

Genetically modified plants are plants of which a heterologous gene encoding a protein of interest has been stably integrated into genome. The expression "heterologous gene encoding a protein of interest" essentially means genes which give the transformed plant new agronomic properties, or genes for improving the agronomic quality of the modified plant.

The method of treatment according to the invention can also be used in the field of protecting storage goods against attack of fungi. According to the instant invention, the term "storage goods" is understood to denote natural substances of vegetable or animal origin and their processed forms, which have been taken from the natural life cycle and for which long-term protection is desired. Storage goods of vegetable origin, such as plants or parts thereof, for example stalks, leafs, tubers, seeds, fruits or grains, can be protected in the freshly harvested state or in processed form, such as pre-dried, moistened, comminuted, ground, pressed or roasted. Also falling under the definition of storage goods is timber, whether in the form of crude timber, such as construction timber, electricity pylons and barriers, or in the form of finished articles, such as furniture or objects made from wood. Storage goods of animal origin are hides, leather, furs, hairs and the like. The combinations according the present invention can prevent disadvantageous effects such as decay, discoloration or mold. Preferably "storage goods" is understood to denote natural substances of vegetable origin and their processed forms, more preferably fruits and their processed forms, such as pomes, stone fruits, soft fruits and citrus fruits and their processed forms.

In the field of protection of technical materials "storage goods" is understood to denote wood. The combination, mixture, agrochemical formulation or composition according to the invention may also be used against fungal diseases liable to grow on or inside timber. The term "timber" means all types of species of wood, and all types of working of this wood intended for construction, for example solid wood, high-density wood, laminated wood, and plywood. The method for treating timber according to the invention mainly consists in contacting one or more compounds according to the invention, or a composition according to the invention; this includes for example direct application, spraying, dipping, injection or any other suitable means.

Among the diseases of plants or crops that can be controlled by the method according to the invention, mention may be made of:

Powdery Mildew Diseases such as Blumeria diseases caused for example by *Blumeria graminis; Podosphaera* diseases caused for example by *Podosphaera leucotricha; Sphaerotheca* diseases caused for example by *Sphaerotheca fuliginea; Uncinula* diseases caused for example by *Uncinula necator*; Rust Diseases such as *Gymnosporangium* diseases caused for example by *Gymnosporangium sabinae*; *Hemileia* diseases caused for example by *Hemileia vastatrix*; *Phakopsora* diseases caused for example by *Phakopsora pachyrhizi* and *Phakopsora meibomiae*; *Puccinia* diseases caused for example by *Puccinia recondite*, and *Puccinia triticina*; *Uromyces* diseases caused for example by *Uromyces appendiculatus*; Oomycete Diseases such as *Bremia* diseases caused for example by *Bremia lactucae*; *Peronospora* diseases caused for example by *Peronospora pisi* and *Peronospora brassicae*; *Phytophthora* diseases caused for example by *Phytophthora infestans*; *Plasmopara* diseases caused for example by *Plasmopara viticola*; *Pseudoperonospora* diseases caused for example by *Pseudoperonospora humuli* and *Pseudoperonospora cubensis*; *Pythium* diseases caused for example by *Pythium ultimum*; Leafspot, Leaf blotch and Leaf Blight Diseases such as *Alternaria* diseases caused for example by *Alternaria solani*; *Cercospora* diseases caused for example by *Cercospora beticola*; *Cladiosporium* diseases caused for example by *Cladiosporium cucumerinum*; *Cochliobolus* diseases caused for example by *Cochliobolus sativus* (Conidiaform: *Drechslera*, Syn: *Helminthosporium*); *Colletotrichum* diseases caused for example by *Colletotrichum lindemuthianum*; *Cycloconium* diseases caused for example by *Cycloconium oleaginum*; *Diaporthe* diseases caused for example by *Diaporthe citri*; *Elsinoe* diseases caused for example by *Elsinoe fawcettii*; *Gloeosporium* diseases caused for example by *Gloeosporium laeticolor*; *Glomerella* diseases caused for example by *Glomerella cingulata*; *Guignardia* diseases caused for example by *Guignardia bidwellii*; *Leptosphaeria* diseases caused for example by *Leptosphaeria maculans*; *Magnaporthe* diseases caused for example by *Magnaporthe grisea*; *Mycosphaerella* diseases caused for example by *Mycosphaerella graminicola* and *Mycosphaerella fijiensis*; *Phaeosphaeria* diseases caused for example by *Phaeosphaeria nodorum*; *Pyrenophora* diseases caused for example by *Pyrenophora teres*; *Ramularia* diseases caused for example by *Ramularia collo-cygni*; *Rhynchosporium* diseases caused for example by *Rhynchosporium secalis*; *Septoria* diseases caused for example by *Septoria apii*; *Typhula* diseases caused for example by *Thyphula incarnate*; *Venturia* diseases caused for example by *Venturia inaequalis*; Root- and Stem Diseases such as *Corticium* diseases caused for example by *Corticium graminearum*; *Fusarium* diseases caused for example by *Fusarium oxysporum*; *Gaeumannomyces* diseases caused for example by *Gaeumannomyces graminis*; *Rhizoctonia* diseases caused for example by *Rhizoctonia solani*; *Oculimacula* (*Tapesia*) diseases caused for example by *Oculimacula Tapesia acuformis*; *Thielaviopsis* diseases caused for example by *Thielaviopsis basicola*; Ear and Panicle Diseases including Maize cob such as *Alternaria* diseases caused for example by *Alternaria* spp.; *Aspergillus* diseases caused for example by *Aspergillus flavus*; *Cladosporium* diseases caused for example by *Cladosporium cladosporioides*; *Claviceps* diseases caused for example by *Claviceps purpurea*; *Fusarium* diseases caused for example by *Fusarium culmorum*; *Gibberella* diseases caused for example by *Gibberella zeae*; *Monographella* diseases caused for example by *Monographella nivalis*; Smut- and Bunt Diseases such as *Sphacelotheca* diseases caused for example by *Sphacelotheca reiliana*; *Tilletia* diseases caused for example by *Tilletia caries*; *Urocystis* diseases *Urocystis occulta*; *Ustilago* diseases caused for example by *Ustilago nuda*; Fruit Rot and Mould Diseases such as *Aspergillus* diseases caused for example by *Aspergillus flavus*; *Botrytis* diseases caused for example by *Botrytis cinerea*; *Penicillium* diseases caused for example by *Penicillium expansum* and *Penicillium purpurogenum*; *Sclerotinia* diseases caused for example by *Sclerotinia sclerotiorum*; *Verticillium* diseases caused for example by *Verticillium alboatrum*; Seed- and Soilborne Decay, Mould, Wilt, Rot and Damping-off diseases; *Fusarium* diseases caused for example by *Fusarium culmorum*; *Phytophthora* diseases caused for example by *Phytophthora cactorum*; *Pythium* diseases caused for example by *Pythium ultimum*; *Rhizoctonia* diseases caused for example by *Rhizoctonia solani*; *Sclerotium* diseases caused for example by *Sclerotium rolfsii*; Canker, Broom and Dieback Diseases such as *Nectria* diseases caused for example by *Nectria galligena*; Blight Diseases such as *Monilinia* diseases caused for example by *Monilinia Taxa*; Leaf Blister or Leaf Curl Diseases including deformation of blooms and fruits such as *Taphrina* diseases caused for example by *Taphrina deformans*; Decline Diseases of Wooden Plants such as Esca disease caused for example by *Phaeomoniella clamydospora* and *Phaeoacremonium aleophilum* and *Fomitiporia mediterranea*; Diseases of Flowers and Seeds such as *Botrytis* diseases caused for example by *Botrytis cinerea*; Diseases of Tubers such as *Rhizoctonia* diseases caused for example by *Rhizoctonia solani*; *Helminthosporium* diseases caused for example by *Helminthosporium solani*; Diseases caused by Bacterial Organisms such as *Xanthomanas* species for example *Xanthomonas campestris* pv. *Oryzae*; *Pseudomonas* species for example *Pseudomonas syringae* pv. *Lachrymans*; *Erwinia* species for example *Erwinia amylovora*.

The combination according to the invention is preferably used to control the following fungal soybean diseases of the Foliage, Upper Stems, Pods and Seeds: *Alternaria* leaf spot (*Alternaria* spec. *atrans tenuissima*), Anthracnose (*Colletotrichum gloeosporoides dematium* var. *truncatum*), Brown spot (*Septoria glycines*), Cercospora leaf spot and blight (*Cercospora kikuchii*), Choanephora leaf blight (*Choanephora infundibulifera trispora* (Syn.)), Dactuliophora leaf spot (*Dactuliophora glycines*), Downy Mildew (*Peronospora manshurica*), Drechslera blight (*Drechslera glycini*), Frogeye Leaf spot (*Cercospora sojina*), Leptosphaerulina Leaf Spot (*Leptosphaerulina trifolii*), Phyllostica Leaf Spot (*Phyllosticta sojaecola*), Pod and Stem Blight (*Phomopsis sojae*), Powdery Mildew (*Microsphaera diffusa*), Pyrenochaeta Leaf Spot (*Pyrenochaeta glycines*), Rhizoctonia Aerial, Foliage, and Web Blight (*Rhizoctonia solani*), Rust (*Phakopsora pachyrhizi*, *Phakopsora meibomiae*), Scab (*Sphaceloma glycines*), Stemphylium Leaf Blight (*Stemphylium botryosum*), Target Spo (*Corynespora cassiicola*);

or fungal Disease of the Roots and Lower Stems for example Black Root Rot (*Calonectria crotalariae*), Charcoal Rot (*Macrophomina phaseolina*), Fusarium Blight or Wilt, Root Rot, and Pod and Collar Rot (*Fusarium oxysporum, Fusarium orthoceras, Fusarium semitectum, Fusarium equiseti*), Mycoleptodiscus Root Rot (*Mycoleptodiscus terrestris*), Neocosmospora (*Neocosmopspora vasinfecta*), Pod and Stem Blight (*Diaporthe phaseolorum*), Stem Canker (*Diaporthe phaseolorum* var. *caulivora*), Phytophthora Rot (*Phytophthora megasperma*), Brown Stem Rot (*Phialophora gregata*), Pythium Rot (*Pythium aphanidermatum, Pythium irregulare, Pythium debaryanum, Pythium myriotylum, Pythium ultimum*), Rhizoctonia Root Rot, Stem Decay, and Damping-Off (*Rhizoctonia solani*), Sclerotinia Stem Decay (*Sclerotinia sclerotiorum*), Sclerotinia Southern Blight (*Sclerotinia rolfsii*), Thielaviopsis Root Rot (*Thielaviopsis basicola*).

In particular, the combination according to the invention is useful for curatively and/or preventively controlling Rust Diseases, such as *Gymnosporangium* diseases, or Rust diseases, which are caused by the harmful fungi of the genera

*Puccinia* (e.g. *Puccinia recondita, Puccinia graminis* and *Puccinia striiformis*), *Uromyces* (e.g. *Uromyces appendiculatus*) and *Phakopsora* (e.g. *Phakopsora pachyrhizi* and *Phakopsora meibomiae*). The combination according to the invention is particularly useful for curatively and/or preventively controlling harmful fungi which are frequently found in legumes (e.g. soybeans) such as *Microsphera diffusa, Cercospora kikuchi, Cercospora sojina, Septoria glycines, Colletotrichum tuncatum, Corynespora cassiicola, Fusarium oxysporum, Fusarium orthoceras, Fusarium semitectum, Fusarium equiseti* and *Sclerotinia sclerotiorum*.

The dose of Prothioconazole and Metominostrobin when used according to the invention is for foliar treatments: from 0.1 to 10,000 g/ha, preferably from 10 to 1,000 g/ha, more preferably from 50 to 300 g/ha; in case of drench or drip application, the dose can even be reduced, especially while using inert substrates like rockwool or perlite; for seed treatment: from 2 to 200 g per 100 kilogram of seed, preferably from 3 to 150 g per 100 kilogram of seed; for soil treatment: from 0.1 to 10,000 g/ha, preferably from 1 to 5,000 g/ha.

The dose may be adapted to the nature of the plant or crop to be treated.

The combination according to the invention may also be used for the preparation of composition useful to curatively or preventively treat human or animal fungal diseases such as, for example, mycoses, dermatoses, *trichophyton* diseases and candidiases or diseases caused by *Aspergillus* spp., for example *Aspergillus fumigatus*.

Furthermore combination according to the invention may also be used to reduce the contents of mycotoxins in the harvested crops and therefore in foods and animal feed stuff made therefrom.

Mycotoxins which can be controlled by the combination or composition according to the invention are for example Deoxynivalenole (DON), Nivalenole, 15-Ac-DON, 3-Ac-DON, T2-und HT2-Toxins, Fumonisines, Zearalenone Moniliformine, Fusarine, Diaceotoxyscirpenole (DAS), Beauvericine, Enniatine, Fusaroproliferine, Fusarenole, Ochratoxines, Patuline, Ergotalcaloides und Aflatoxines, which are caused for example by the following fungal diseases: *Fusarium* spec., like *Fusarium acuminatum, F. avenaceum, F. crookwellense, F. culmorum, F. graminearum* (*Gibberella zeae*), *F. equiseti, F. fujikoroi, F. musarum, F. oxysporum, F. proliferatum, F. poae, F. pseudograminearum, F. sambucinum, F. scirpi, F. semitectum, F. solani, F. sporotrichoides, F. langsethiae, F. subglutinans, F. tricinctum, F. verticillioides* and others but also by *Aspergillus* spec., *Penicillium* spec., *Claviceps purpurea, Stachybotrys* spec. and others.

As before mentioned, Prothioconazole and Metominostrobin, preferably as a mixture, agrochemical formulation or composition are particularly suitable for the treatment of seed. The control of pests by treatment of the seeds of plants has been known for a considerable time and is the object of continuous improvement. However, there are a number of problems in the treatment of seed that cannot always be satisfactorily solved. Therefore there is a need to develop methods for the protection of seeds and germinating plants which makes the additional application of plant protection agents after seeding or after germination of the plants superfluous. There is also the need to optimize the amount of the applied active compounds such that the seed and the germinating plants are protected against infestation by pathogens as best as possible without the plants themselves being damaged by the active compounds applied. In particular, methods for the treatment seed should also take into account the intrinsic (insecticidal) properties of transgenic plants in order to achieve optimal protection of the seed and germinating plants with a minimal expenditure of plant protection agents.

Therefore, the present invention relates especially to a method for the protection of seed and germinating plants from infestation with pathogens in that the seed is treated with Prothioconazole and Metominostrobin, preferably as a mixture, agrochemical formulation or composition. In addition the invention relates also to the use of Prothioconazole and Metominostrobin, preferably as a mixture, agrochemical formulation or composition for the treatment seed for protection of the seed and the germinating plants. Furthermore the invention relates to seed which was treated with Prothioconazole and Metominostrobin, preferably as a mixture, agrochemical formulation or composition.

One of the advantages of the invention is that the treatment of the seed not only protects the seed itself but also the plants which emerge after sprouting. This is due to the special systemic properties of Prothioconazole and Metominostrobin. Thus, the direct treatment of the culture at the time of sowing or shortly thereafter can be omitted.

It is also be regarded as advantageous that Prothioconazole and Metominostrobin, preferably as a mixture, agrochemical formulation or composition can be used on transgenic seeds without disabling the expression of the specific protein which is directed to combat certain pests, in the plants which emerged from the treated seeds.

By treatment of such transgenic seed with Prothioconazole and Metominostrobin, preferably as a mixture, agrochemical formulation or composition certain pests can already be controlled by expression of the, for example, insecticidal protein, and it is additionally surprising that a synergistic activity supplementation occurs with the agents of the invention, which improves still further the effectiveness of the protection from infestation.

The combination of Prothioconazole and Metominostrobin, preferably as a mixture, agrochemical formulation or composition is suitable for the protection of seed of plant varieties of all types as already described which are used in agriculture, in greenhouses, in forestry, in garden construction or in vineyards. In particular, seed of maize, peanut, canola, rape, poppy, olive, coconut, cacao, soy, cotton, beet, (e.g. sugar beet and feed beet), rice, millet, wheat, barley, oats, rye, sunflower, sugar cane or tobacco. The combination of Prothioconazole and Metominostrobin, preferably as a mixture, agrochemical formulation or composition, is also suitable for the treatment of the seed of fruit plants and vegetables as previously described. Particular importance is attached to the treatment of the seed of maize, soy, cotton, wheat and canola or rape.

In view of the treatment of transgenic seed, seeds of plants which generally contain at least one heterologous gene that controls the expression of a polypeptide (often a protein) with special insecticidal properties are preferred. The heterologous gene in transgenic seed can originate from microorganisms such as *Bacillus, Rhizobium, Pseudomonas, Serratia, Trichoderma, Clavibacter, Glomus* or *Gliocladium*. The present invention is particularly suitable for the treatment of transgenic seed that contains at least one heterologous gene that originates from *Bacillus* sp. and whose gene product exhibits activity against the European corn borer and/or western corn rootworm. Particularly preferred is a heterologous gene that originates from *Bacillus thuringiensis*.

Within the context of the present invention Prothioconazole and Metominostrobin are applied to the seed alone or in a suitable formulation. The seed treatment can be carried out at any time between harvest and sowing. Preferably the seed treatment is carried out with seeds being in a biological stable state, so that no damage occurs during treatment. Seed may be used which is separated from the plant and has been freed of spadix, husks, stalks, pods, wool or fruit flesh. Also, seed can be used that was harvested, purified, and dried to a moisture content of below 15% w/w. Alternatively, seed treated first with water after drying and then dried again can also be used.

When treating seeds, care must be taken that the quantity/amount of Prothioconazole and Metominostrobin and the further additive applied to the seed does not impair the germination of the seed and/or damage the emerging plant. The latter frequently occurs when the active ingredients show phytotoxic effects when applied in a certain amount.

Prothioconazole and Metominostrobin, preferably as a mixture, agrochemical formulation or composition can be applied directly, that is without containing additional components and without being diluted. It is normally preferred to apply Prothioconazole and Metominostrobin, to the seed in the form of a suitable formulation. Suitable formulations and methods for seed treatment are known to the person skilled in the art and are described, for example, in the following documents: U.S. Pat. No. 4,272,417 A, U.S. Pat. No. 4,245,432 A, U.S. Pat. No. 4,808,430 A, U.S. Pat. No. 5,876,739 A, US 2003/0176428 A1, WO 2002/080675 A1, WO 2002/028186 A2.

The good fungicidal activity of the combination of Prothioconazole and Metominostrobin is evident from the example below. While the individual active compounds exhibit weaknesses with regard to the fungicidal activity, the combinations have an activity which exceeds a simple addition of activities.

A synergistic effect of fungicides is always present when the fungicidal activity of the active compound combinations exceeds the total of the activities of the active compounds when applied individually.

The expected activity for a given combination of two active compounds can be calculated as follows (cf. Colby, S. R., "Calculating Synergistic and Antagonistic Responses of Herbicide Combinations", Weeds 15, pages 20-22, 1967):

If

X is the efficacy, when applying the active compound A at a rate of application of active compound of m ppm, Y is the efficacy, when applying the active compound B at a rate of application of active compound of n ppm, E is the expected efficacy, when applying the active compounds A and B at rates of application of active compound of m and n ppm, then $$E = X + Y - \frac{X \cdot Y}{100}$$

The degree of efficacy, expressed in % is denoted. 0% means an efficacy which corresponds to that of the control while an efficacy of 100% means that no disease is observed.

If the actual fungicidal activity exceeds the calculated value, then the activity of the combination is superadditive, i.e. a synergistic effect exists. In this case, the efficacy which was actually observed must be greater than the value for the expected efficacy (E) calculated from the above-mentioned formula.

The invention is illustrated by the following example.

BIOLOGICAL EXAMPLE 1

Phakopsora Test (Soybeans)/Protective

Solvent: 28.5 parts by weight of acetone
Emulsifier: 1.5 parts by weight of polyoxyethylene alkyl phenyl ether To produce a suitable preparation of active compound, 1 part by weight of active compound or active compound combination is mixed with the stated amounts of solvent and emulsifier, and the concentrate is diluted with water to the desired concentration.

To test for protective activity, young plants are sprayed with the preparation of active compound or active compound combination at the stated rate of application. After the spray coating has dried on, the plants are placed in a greenhouse at a temperature of approximately 23° C. and a relative atmospheric humidity of approximately 70%.

1 day after spraying, the plants are inoculated with an aqueous spore suspension of the causal agent of soybean rust (*Phakopsora pachyrhizi*). The plants are then placed in a greenhouse at approximately 20° C. and a relative atmospheric humidity of approximately 80%. The test is evaluated 11 days after the inoculation. 0% means an efficacy which corresponds to that of the control, while an efficacy of 100% means that no disease is observed.

From the following tables it can be seen that the observed activity of the combination according to the invention is greater than the calculated activity, i.e. a synergistic effect is present.

Phakopsora Test (Soybeans)/Protective

| Active compound | Rate of application of active compound in ppm | Efficacy in % |
| --- | --- | --- |
| Metominostrobin | 5 | 20 |
|  | 2.5 | 0 |
| Prothioconazole | 0.5 | 50 |
|  | 0.1 | 20 |

| | Ratio of the mixture | Rate of application of active compound in ppm | Actual efficacy | Expected value, calculated using Colby's formula |
| --- | --- | --- | --- | --- |
| Metominostrobin + Prothioconazole | 50:1 | 5 + 0.1 | 65 | 36 |

-continued

| | Ratio of the mixture | Rate of application of active compound in ppm | Actual efficacy | Expected value, calculated using Colby's formula |
|---|---|---|---|---|
| Metominostrobin + Prothioconazole | 5:1 | 2.5 + 0.5 | 80 | 50 |
| Metominostrobin + Prothioconazole | 25:1 | 2.5 + 0.1 | 50 | 20 |

BIOLOGICAL EXAMPLE 2

Blumeria Test (Wheat)/Preventive

| Solvent: | 49 parts by weight of n,n-dimethylacetamid |
|---|---|
| Emulsifier: | 1 part by weight of alkylaryl polyglycol ether |

To produce a suitable preparation of active compound, 1 part by weight of active compound or active compound combination is mixed with the stated amounts of solvent and emulsifier, and the concentrate is diluted with water to the desired concentration.

To test for preventive activity, young plants are sprayed with the preparation of active compound or active compound combination at the stated rate of application. After the spray coating has been dried, the plants are dusted with spores of *Blumeria graminis* fsp. *tritici*. The plants are placed in the greenhouse at a temperature of approximately 18° C. and a relative atmospheric humidity of approximately 80% to promote the development of mildew pustules.

The test is evaluated 7 days after the inoculation. 0% means an efficacy which corresponds to that of the control, while an efficacy of 100% means that no disease is observed.

From the following tables it can be seen that the observed activity of the combination according to the invention is greater than the calculated activity, i.e. a synergistic effect is present.

Blumeria Test (Wheat)/Preventive

BIOLOGICAL EXAMPLE 3

*Sphaerotheca* Test (Cucumbers)/Protective

| Solvent: | 24.5 parts by weight of acetone |
|---|---|
| | 24.5 parts by weight of dimethylacetamide |
| Emulsifier: | 1 part by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for protect activity, young plants are sprayed with the preparation of active compound at the stated rate of application. After the spray coating has dried on, the plants are inoculated with an aqueous spore suspension of *Sphaerotheca fuliginea*. The plants are then placed in a greenhouse at approximately 23° C. and a relative atmospheric humidity of approximately 70%.

The test is evaluated 7 days after the inoculation. 0% means an efficacy which corresponds to that of the control, while an efficacy of 100% means that no disease is observed.

From the following tables it can be seen that the observed activity of the combination according to the invention is greater than the calculated activity, i.e. a synergistic effect is present.

*Sphaerotheca* Test (Cucumbers)/Protective

| Active compound | Rate of application of active compound in ppm | Efficacy in % |
|---|---|---|
| Metominostrobin | 62.5 | 50 |
| Prothioconazole | 62.5 | 13 |

| Active compound | Rate of application of active compound in ppm | Efficacy in % |
|---|---|---|
| Metominostrobin | 2 | 0 |
| Prothioconazole | 2 | 65 |

| | Ratio of the mixture | Rate of application of active compound in ppm | Actual efficacy | Expected value, Calculated using Colby's formula |
|---|---|---|---|---|
| Metominostrobin + Prothioconazole | 1:1 | 62.5 + 62.5 | 88 | 57 |

| | Ratio of the mixture | Rate of application of active compound in ppm | Actual efficacy | Expected value, calculated using Colby's formula |
|---|---|---|---|---|
| Metominostrobin + Prothioconazole | 1:1 | 2 + 2 | 87 | 65 |

The invention claimed is:

1. A composition comprising Prothioconazole

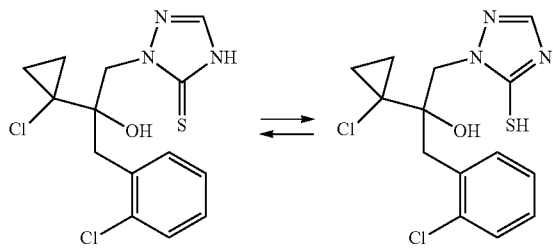 [SMILES: OC(Cc1ccccc1Cl)(Cn1nc[nH]c1=S)C1(Cl)CC1 ; OC(Cc1ccccc1Cl)(Cn1ncnc1S)C1(Cl)CC1]

and Metominostrobin

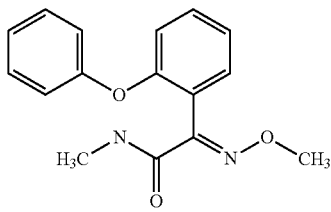 [SMILES: CNC(=O)/C(=N/OC)c1ccccc1Oc1ccccc1]

in a weight ratio from 1:50 to 50:1.

2. A mixture or an agrochemical formulation composition according to claim 1.

3. A method of controlling phytopathogenic fungi and/or microorganisms of a plant or crop comprising applying the composition according to claim 1 to the plant or crop.

4. The method according to claim 3, wherein the phytopathogenic fungi and/or microorganisms are selected from the group consisting of the genuses *Puccinia, Uromyces* and *Phakopsora*.

5. The composition according to claim 1 further comprising a seed.

6. A method of controlling phytopathogenic fungi and/or microorganisms of plants and crops comprising applying prothioconazole and metominostrobin together to the plants, plant parts or seed of the plants.

7. The method according to claim 6, wherein the phytopathogenic fungi and/or microorganisms are selected from the group consisting of the genuses *Puccinia, Uromyces* and *Phakopsora*.

* * * * *